(12) United States Patent
Kumar et al.

(10) Patent No.: US 9,241,948 B2
(45) Date of Patent: Jan. 26, 2016

(54) READY TO BE INFUSED GEMCETABINE SOLUTION

(71) Applicant: SUN PHARMACEUTICAL INDUSTRIES LTD., Mumbai (IN)

(72) Inventors: Samarth Kumar, Vadodara (IN); Prashant Kane, Vadodara (IN); Alok B. Namdeo, Vadodara (IN); Subhas B Bhowmick, Vadodara (IN); Kirti Ganorkar, Mumbai (IN)

(73) Assignee: Sun Pharmaceutical Industries Ltd., Mumbai (IN)

( * ) Notice: Subject to any disclaimer, the term of this patent is extended or adjusted under 35 U.S.C. 154(b) by 66 days.

(21) Appl. No.: 13/871,438

(22) Filed: Apr. 26, 2013

(65) Prior Publication Data

US 2013/0288994 A1 Oct. 31, 2013

(30) Foreign Application Priority Data

Apr. 27, 2012 (IN) .......................... 1334/MUM/2012

(51) Int. Cl.
*A61K 31/7068* (2006.01)
*A61K 9/00* (2006.01)
*A61K 47/02* (2006.01)

(52) U.S. Cl.
CPC ........... *A61K 31/7068* (2013.01); *A61K 9/0019* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 5,135,498 A * | 8/1992 | Kam | A61M 5/1483 128/DIG. 12 |
| 2004/0147486 A1* | 7/2004 | Szymanski et al. | 514/102 |
| 2005/0031679 A1* | 2/2005 | Unger | A61K 9/1278 424/450 |
| 2006/0046964 A1* | 3/2006 | Morneau | 514/12 |
| 2006/0154891 A1* | 7/2006 | Schridde et al. | 514/49 |
| 2008/0102030 A1* | 5/2008 | Decuzzi | A61K 9/143 424/9.1 |
| 2011/0003777 A1* | 1/2011 | Sehested et al. | 514/155 |

* cited by examiner

*Primary Examiner* — Eric Olson
*Assistant Examiner* — Dale R Miller
(74) *Attorney, Agent, or Firm* — Sughrue Mion, PLLC (57) ABSTRACT

A large volume infusion dosage form of gemcitabine, comprising a stable large volume solution of gemcitabine or its pharmaceutically acceptable salt in an aqueous vehicle filled in a large volume infusion container, wherein the solution is ready-to-be-infused.

10 Claims, 3 Drawing Sheets

READY TO BE INFUSED GEMCETABINE SOLUTION

FIELD OF INVENTION

The present invention provides a large volume infusion dosage form of gemcitabine, comprising a stable large volume solution of gemcitabine or its pharmaceutically acceptable salt in an aqueous vehicle filled in a large volume infusion container, wherein the solution is ready-to-be-infused.

BACKGROUND OF INVENTION

Gemcitabine, a synthetic pyrimidine nucleoside antineoplastic agent causes cellular arrest by inhibiting ribonucleotide reductase and DNA synthesis. It is used in the treatment of the various types of cancer such as non-small cell lung cancer (NSCLC) when given alone or together with cisplatin, pancreatic cancer, breast cancer, when given together with paclitaxel, in treatment of ovarian cancer when given together with carboplatin and in treatment of bladder cancer when given together with cisplatin. The existing parenteral gemcitabine hydrochloride injections are available either in the form of a sterile lyophilized powder or a concentrated solution. Neither of these forms can be directly administered to a patient, rather they require manipulation. It is extremely important that no microbial contamination occurs during this manipulation and the sterile nature of the product is preserved. Thus the procedure requires that the hospital staff follow recommended sterile technique. Deviation from recommended sterile technique poses a risk to the patient. Moreover, manual manipulation such as steps of reconstitution, dilution and incorporation into a sterile aqueous vehicle suitable for intravenous infusion can result in the wrong dose being administered or even in the error of infusing different drug in cases where the patient is prescribed combination chemotherapy with multiple drugs or other medication errors.

Gemcitabine preparations required for parenteral administration are currently available in the form of lyophilizates (Gemzar®), which must be reconstituted before administration to the patient. However, these freeze-dried preparations have considerable disadvantages. First of all, the process of preparing these lyophilisates is complicated and costly. Secondly, reconstitution requires additional working steps and undesirable risks of personnel involved. In particular, reconstitution of drug solutions from a dry substance can result in what has been called the 'spray-back effect,' which may result in further contamination and risk of personnel. As described above, other errors in handling can lead to serious problems such as deviation in the concentration of active substance, or microbial contamination. Further, it is reported (See Physician Desk Reference, Gemzar) that the maximum concentration for Gemzar® upon reconstitution, is 40 mg/mL. It is reported that at concentrations greater than 40 mg/mL may result in incomplete dissolution, and therefore should be avoided. Further, for Gemzar® like products which require reconstitution, normal safety precautions need to be observed when preparing and disposing of the infusion solution. Handling of such products needs to be carried out in a safety box. Use of protective coats and gloves is suggested. Particularly, the package insert states that if no safety box is available, the equipment should be supplemented with a mask and protective glasses. Further, the pack insert provides precaution that during the use of the concentrate product, there are chances that the preparation can come into contact with the eyes, which may cause serious irritation. Again, since there is a human intervention, there are chances that the solution can be spilled on the skin.

A study of prior art reveals that attempts have been made to solve the above described problems but none has led to a large volume infusion dosage form of gemcitabine wherein the dosage form is a stable solution of a gemcitabine or its pharmaceutically acceptable salt in an aqueous vehicle in a large volume infusion container. For example, United States Patent Application Number US20060089328 describes an injectable pharmaceutical composition comprising a solution of gemcitabine having a pH of about 3.5 to about 10 and a gemcitabine concentration of about 0.5 mg/ml to about 16 mg/ml. This patent application describes a solution of gemcitabine which is prepared by aseptic filtration having 2 ml filled aseptically into 2 ml perforable stopper vials. Anohter prior art, US20060154891, mentions the gemcitabine solutions to be ready-to-use and gemcitabine concentrates. However, it is to be noted that the "ready-to-use" solution is the one which is not reconstituted from a solid, such as a crystalline or an amorphous solid or a lyophilisate, immediately before it is administered to a patient. Thus, this prior art teaches a ready to use solution having an intervening step of dilution or mixing before administration.

It is important to note that the concentrate of the prior art, needs to be withdrawn and diluted with a vehicle suitable for infusion for suitable dose. Risks associated with such manipulation, for example, the appearance of particulates or crystalline drug in the perfusate remains a possibility. Further, for higher doses such as 1500 mg or above, more than one vials of prior art either having the preconcentrate or the lyophilized powder, may be required to achieve the dose as against the single ready to be infused solution of the present invention which can be immediately given to the patients, with accurate dose. The present invention thus enables the user to avoid steps of using more than one vial, a small volume parenteral container, to arrive at higher doses that are not equivalent in a single vial.

PCT publication Number WO2007037793 (herein after referred to as WO'793) teaches flexible containers having multiple chambers so that incompatible solutions in different compartments are isolated and the container allow selective sterile admixing to form a ready-to-infuse formulation prior to administration. Thus, a stable ready-to-infuse solution is absent in any of the chambers, rather a solution which may be unstable over time is formed before administration and administered immediately.

A particular problem encountered with a large volume gemcitabine solution is disclosed in Xu et al (J. Am. Pharm. Assoc., Vol 39, No 4, July/August 1999, page no 509-513). The authors found that when lyophilized gemcitabine (Gemzar®—Eli Lilly and Company) was reconstituted with aqueous vehicles and the infusion solution was stored at 4° C. for 14 days or more, crystals of gemcitabine appeared. These crystals did not dissolve upon warming to room temperature. Thus, the prior large volume infusion solution formed on reconstitution was unstable. The present inventors were confounded with the same problem and infusion solutions of gemcitabine showed appearance of crystals or particulates when they were stored at 2-8° C. or at room temperatures. The present inventors have now surprisingly found large volume infusion dosage form of gemcitabine wherein the dosage form is a "stable solution" of gemcitabine or its pharmaceutically acceptable salt in an aqueous vehicle in a large volume infusion container and wherein the solution is ready-to-infuse. The large volume infusion dosage form of the present invention is "stable" and "ready to be infused" gemcitabine large volume solution meaning thereby that the solution is stable over time, is sterile, has a volume in excess of 100 ml and can be directly infused intravenously without any intervening step of reconstitution or dilution or mixing.

Thus, the present invention can be said to solve the unmet need of ready to be infused solution dosage form of gemcitabine, which is a large volume infusion dosage form of gemcitabine wherein the dosage form is a solution of a gemcitabine or its pharmaceutically acceptable salt in an aqueous vehicle in a large volume infusion container and wherein the solution is ready-to-be infused. The present inventors surprisingly found that a large volume infusion solution in a large volume infusion container was stable after it was subjected to terminal sterilization. The gemcitabine solution of the invention is stable for extended periods of time in the liquid state, without having to undergo a step of freeze-drying or reconstitution. That is it represents a substantial advancement over the art, and a major convenience to potential patients. The ready to infuse solution avoids the inconvenience of diluting a concentrated small volume gemcitabine hydrochloride parenteral formulation into infusion diluents prior to infusion, as well as eliminates the risk of microbiological contamination during aseptic handling and any potential calculation or dilution error.

SUMMARY OF THE INVENTION

The present invention provides a large volume infusion dosage form of gemcitabine, comprising a stable large volume solution of gemcitabine or its pharmaceutically acceptable salt in an aqueous vehicle filled in a large volume infusion container, wherein the solution is ready-to-be-infused.

A kit comprising a large volume infusion dosage form comprising a stable large volume solution of gemcitabine or its pharmaceutically acceptable salt in an aqueous vehicle filled in a large volume polymeric infusion container covered with a secondary packaging system, wherein the solution is ready-to-be-infused.

DETAILED DESCRIPTION OF THE INVENTION

Figure 1:
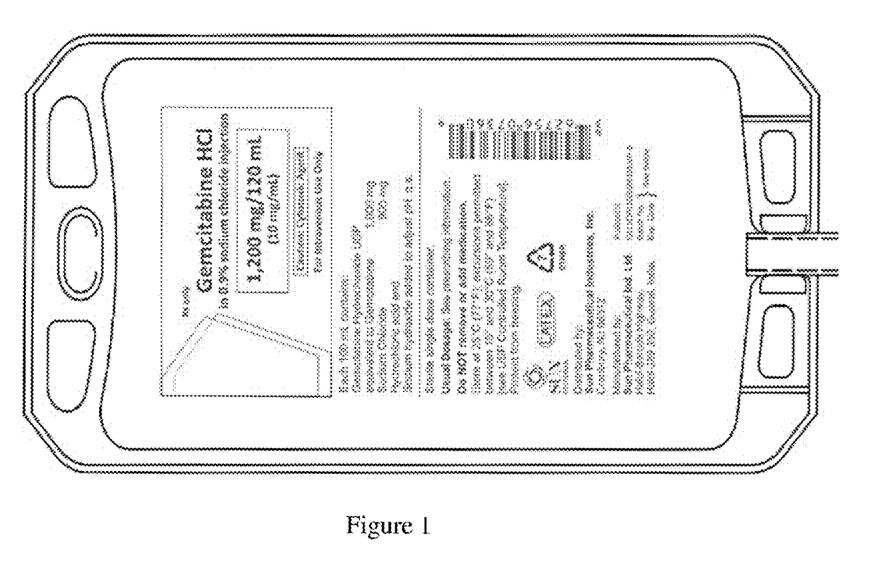
FIG. 1 shows a 'ready to be infused' large volume infusion dosage form of gemcitabine hydrochloride solution of 10 mg per ml gemcitabine solution in a volume of 180 ml which provides a total dose of 1800 mg of gemcitabine. This can be administered at an infusion rate of 3 ml per minute for a period of 60 minutes or can be infused at 6 ml per minute for a period of 30 minutes.
Figure 2:
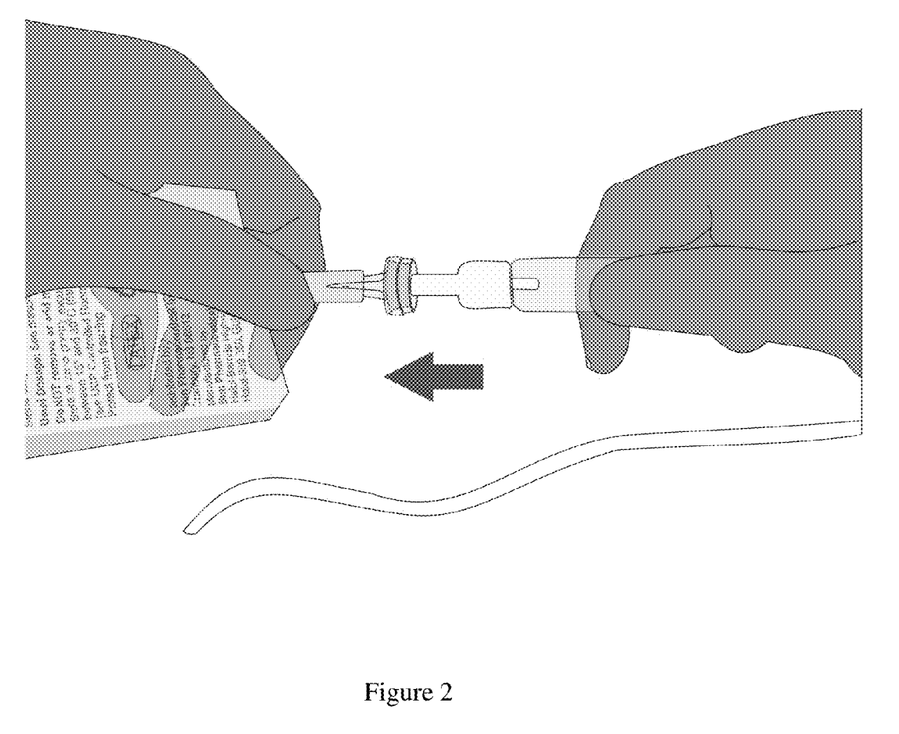
FIG. 2 shows the 'ready to be infused' large volume infusion dosage form of gemcitabine hydrochloride solution presented in the infusion bag having a port for cannulating to the IV tubes and can be directly administered without any intervening step of reconstitution or dilution.
Figure 3:
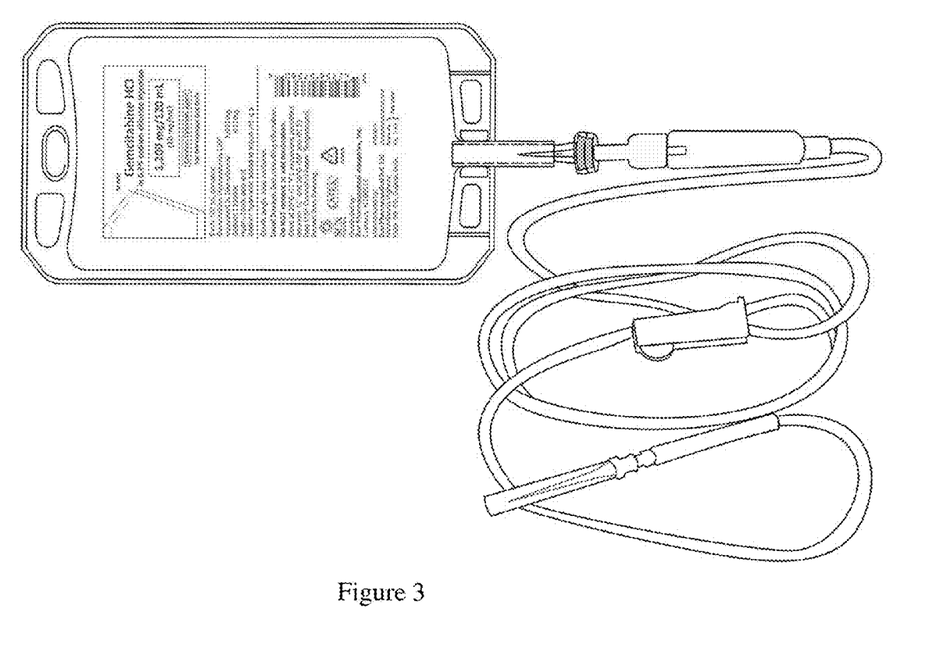
FIG. 3 shows the cannulated infusion container containing ready to infuse gemcitabine hydrochloride solution of 180 ml of 10 mg per ml.

According to the present invention, the pharmaceutical solution is referred to as a 'ready to infuse' solution or a 'ready-to-be-infused' solution, i.e., the solution does not require any prior dilution or reconstitution or mixing before administration. This attribute of the present invention makes the pharmaceutical solution extremely user friendly. It is envisaged that it will be possible to use the product of the invention to directly infuse, intravenously, the solution contained therein without the need for any intervening step of reconstitution or dilution or mixing.

The term 'stable', as used in the context of this application, means remaining in a state or condition that is suitable for administration to a patient. In particular, a "stable solution" is intended to refer to a solution which when stored at 2° C. to 8° C. or at room temperature, for a period of time, is physically stable, for example, it does not show the appearance of visible particulates and is also chemically stable. The term "chemically stable" as used herein means that when the dosage form is stored at room temperature or at 2° C. to 8° C., the impurities such as those resulting from chemical reaction in solution remains within acceptable limits over a long term storage. It is intended that the period of time over which the solution is stable for 12 months or 24 months. In one preferred embodiment, the solutions according to the present invention have been found to be stable when maintained at room temperature or refrigerated condition for at least 24 months. It was found that the solutions are generally stable at refrigerated conditions or room temperature for 24 to 36 months. The large volume infusion dosage form of the present invention consists of gemcitabine or its pharmaceutically acceptable salt, as the sole active ingredient.

The term 'sterile' solution dosage form, as used in the context of this application, means a dosage form that has been brought to a state of sterility and has not been subsequently exposed to microbiological contamination, i.e. the sterility of the container holding the sterile composition has not been compromised. Sterile compositions are generally prepared by pharmaceutical manufacturers in accordance with current Good Manufacturing Practice ("cGMP") regulations of the U.S. Food and Drug Administration.

The term "large volume" refers to a volume of at least 100 ml, for example in the range of from 100 ml to 500 ml, preferably 110 ml to 250 ml.

According to the present invention, the volume of the solution filled in the infusion container can be tailored to cater single dose of gemcitabine hydrochloride as per the prescription. In one embodiment, gemcitabine hydrochloride (expressed as free base) solution at a concentration of 10 mg/ml is dispensed into the infusion bottles in variable volumes corresponding to a dose of 1000 mg to 3000 mg per infusion container. In another embodiment, the concentration of gemcitabine hydrochloride is 15 mg/ml. It may be noted that depending on the concentration of gemcitabine hydrochloride, variable volumes of the solution can be filled in the infusion containers, in order to achieve the desired dose of gemcitabine hydrochloride per container, which will correspond to a single dose. For example, the concentration of gemcitabine hydrochloride can range from 5 mg per ml to 20 mg per ml, preferably, 8 mg per ml to 16 mg per ml. According to the present invention, the large volume solution of gemcitabine hydrochloride is present at having a concentration ranging from 5 mg per ml to 20 mg per ml, preferably 8 mg to 18 mg per ml. Correspondingly, the volume of solution per container can range from about 100 ml to about 500 ml.

For example, a 10 mg per ml gemcitabine hydrochloride (expressed as free base) solution can be provided in different volumes such as 100 ml, 160 ml, 200 ml, 260 ml or 300 ml to provide 1000 mg, 1600 mg, 2000 mg, 2600 mg or 3000 mg respectively.

The large volume infusion solution of the present invention can include, inert excipients such as tonicity adjusting agents, buffers. The solution does not include presence of saccharide component, e.g. D-sorbitol, mannitol, sucrose. So also, the solution does not require co-solvents like alcohol, such as ethanol and glycol, e.g. propylene glycol, polyethylene glycol, trimethylene glycol and butylene glycol.

The pH of the solution of the present invention ranges from about 6.0 to about 8.0. The suitable physiologically acceptable buffering agents such as phosphate, Tris® may be included in the solution to maintain the pH. Buffering agents may be present in the solution in a concentration that depends on the concentration of gemcitabine hydrochloride. Suitable tonicity agents, when used, are compatible with the pH requirements include, but are not limited to, one or more of sodium chloride, calcium chloride and potassium chloride. Preferred is sodium chloride. The solution of the present invention may contain 1 to 100 mg/mL tonicity agents; preferably 4 to 60 mg/mL sodium chloride, more preferably 4 to 10 mg/mL sodium chloride.

Various doses of gemcitabine hydrochloride solution can be provided by the gemcitabine hydrochloride ready to be infused solution of the present invention of a specific concentration, but in different volumes. The concentration and volume per container is optimized such that the ready to infuse solution is administered to the patient in an acceptable time limit of 60 minutes as a very safe rate of infusion which is about 8 ml per minute or less. The product is sterile, stable and ready to infuse. This form of ready to infuse solution avoids the inconvenience of diluting a concentrated small volume gemcitabine hydrochloride parenteral formulation into infusion diluents prior to infusion, as well as eliminates the risk of microbiological contamination during aseptic handling and any potential calculation or dilution error.

The ready to be infused solution dosage form according to the present invention can be held in any suitable large volume single compartment container. Suitable polymeric single compartment containers include, for example, glass or polymeric vials, ampoules, syringes, infusion bags or infusion bottles with sizes ranging from 100 ml to 500 ml. The large volume parenteral presentations can be contained in infusion bags or bottles. Polymeric single compartment containers are preferably flexible and can contain or be free of polyvinylchloride (PVC). In one of the embodiment, ready to be infused solution dosage form contains 160 ml and 170 ml of the stable large volume solution of gemcitabine hydrochloride in an aqueous vehicle. In this embodiment, the material of construction of the infusion container is is a multilayer M312 with one tube polyolefins/EVA: 6.2/8.2±0.15 MM sippex. In another embodiment, the material of construction of the infusion container is a multilayer M312 with one tube polyolefins/EVA: 6.2/8.2±0.15 MM sippex. The infusion containers include minitulipe stopper made up of M95A spike port with chlorobutyl (Latex free) 6321 GS joint sippex 323.

The present invention also provides a kit comprising a large volume infusion dosage form comprising a stable large volume solution of gemcitabine or its pharmaceutically acceptable salt in an aqueous vehicle filled in a large volume infusion polymeric container covered with a secondary packaging system, wherein the solution is ready-to-be-infused. The polymeric containers are provided with a moisture barrier as a secondary packaging system to prevent the loss of water during storage and to further ensure the stability of the solution. The secondary packaging not only provides a moisture barrier but it also provides additional protection which is important as gemcitabine is a cytotoxic agent. The additional packaging also protects the infusion containers from being tampered or misused and can help to provide unique identity to the product. In one embodiment, the secondary packaging is of an aluminum over-pouch. It can protect the solution from photolytic degradation. Furthermore the container used is capable of withstanding heat sterilization in the filled and unfilled state, preferably moist heat sterilization. In one embodiment, the kit comprises a large volume infusion dosage form wherein the infusion container is filled with 160 ml of stable large volume solution of 10 mg/ml of gemcitabine or its pharmaceutically acceptable salt in an aqueous vehicle and provides a dose of 1600 mg of gemcitabine hydrochloride per container. In another embodiment, the kit comprising a large volume infusion dosage form wherein the infusion container includes 170 ml of stable large volume solution of 10 mg/ml of gemcitabine hydrochloride in an aqueous vehicle which provides a dose of 1700 mg of gemcitabine hydrochloride per container. In yet another embodiment, the kit comprising a large volume infusion dosage form wherein the infusion container includes 180 ml of stable large volume solution of 10 mg.ml of gemcitabine hydrochloride in an aqueous vehicle which provides a dose of 1800 mg of gemcitabine hydrochloride per container. In another similar embodiment, the kit comprises a large volume infusion dosage form wherein the infusion container includes 190 ml of stable large volume solution of gemcitabine hydrochloride in an aqueous vehicle and provides a dose of 1900 mg of gemcitabine hydrochloride per container.

In one embodiment, a product comprising a large volume infusion dosage form of gemcitabine aqueous solution is present in a flexible plastic bag container. This large volume infusion dosage form of the present invention is safe as determined by the USP 29 chapter 87 test. The USP 29 chapter 87, tests are designed to determine the biological reactivity of mammalian cell cultures following contact with the elastomeric plastics and other polymeric materials with direct or indirect patient contact. There are three tests for in vitro biological reactivity and they are: i) Agar diffusion test, ii) Direct contact test and iii) Elution test. In context with the present invention, the agar test has been performed for in vitro biological reactivity. This test is designed for elastomeric closures in a variety of shapes. Here closure is platinum cured silicone tube. The agar layer acts as a cushion to protect the cells from mechanical damage while allowing the diffusion of leachable chemical from polymeric specimens. Extracts of the materials are applied to a piece of filter paper and it was placed on the prepared thin monolayer cell culture of agar and incubated for not less than 24 hours at 37±1°, preferably in humidified incubator containing 5±1% of carbon dioxide. The biological reactivity is described and rated on the scale of 0 to 4. The sample meets requirements of the test if the response to the sample preparation is not greater than grade 2 (mildly reactive) and the test performed met the requirements i.e. grade is not more than 2.

In another aspect, the present invention provides a method of treating cancer, which method comprises administering ready to be infused sterile solution dosage form of gemcitabine hydrochloride wherein the gemcitabine solution administered to a cancer patient by intravenous infusion, wherein the solution is infused without any intervening step of reconstitution or dilution. Particularly, the present invention provides a method of treating cancer, which method comprises administering a sterile, stable large volume ready to be infused solution comprising 5 mg per ml to 20 mg per ml of gemcitabine hydrochloride (expressed as free base) wherein the gemcitabine hydrochloride is administered at 1000 mg per $m^2$ to 3000 mg per $m^2$ to a cancer patient by intravenous infusion for a period of about 30 minutes to about 1 hour, wherein the solution is infused without any intervening step of reconstitution or dilution. Particularly, the present invention provides an aqueous, stable, sterile pharmaceutical solution of gemcitabine hydrochloride suitable for parenteral administration and having a pH between 6 and 8 comprising in solution 5 mg to 20 mg gemcitabine hydrochloride(expressed as free base) per ml of the solution. The solution is storage-stable (both refrigerated and room temperature), capable of being aseptically-filled and heat-sterilized. The infusion container contains gemcitabine hydrochloride solution at a concentration and in a volume such that there is no requirement of dilution before administration i.e. the solution can be directly infused from the large volume infusion container.

In one embodiment, the large volume infusion dosage form of the present invention provides a recommended dose of 1250 mg/m$^2$ gemcitabine for breast cancer patients. In order to provide this dose, the infusion dosage form is tailored to contain 125 mL of ready to be infused solution of gemcitabine hydrochloride at a concentration of 10 mg/mL in a large volume infusion container. Similarly, the dosage form of the present invention provides 1000 mg/m$^2$ of gemcitabine, an approved dose for ovarian, non small cell lung cancer and pancreatic cancer.

The large volume infusion dosage form of the present invention can be prepared by a process comprises the steps of dissolving of gemcitabine hydrochloride in water for injection to achieve a concentration of 5 mg to 20 mg of gemcitabine base in one milliliter of the solution. The pH may be adjusted to 6 or above with the addition of a base and/or an acid, the solution is then filled in an infusion container and filled infusion container is then terminally sterilized. Terminal sterilization can be achieved by y-irradiation, e-Beam, natural light, microwave heat sterilization such as moist heat sterilization. The terminal sterilization may be steam sterilization or may be heat sterilization or a combination thereof. In one embodiment, the present invention provides a ready to be infused sterile solution dosage form which is terminally steam sterilized. Particularly, the present invention provides the use of terminal heat sterilization to destroy all viable microorganisms within the final, sealed container. Advantageously the heat sterilization is terminal heat sterilization. An autoclave may be used to accomplish terminal heat-sterilization of drug products in their final packaging. Typical autoclave cycles in the pharmaceutical industry to achieve terminal sterilization of the final product are 121° C. for 15 minutes. The gemcitabine hydrochloride composition of the present invention can be autoclaved at a temperature ranging from 110° C. to 150° C. (preferably from 115° C. to 130° C., and more preferably from 120 to 125° C.) for a period of time ranging from 5 to 40 minutes (preferably 10 to 30 minutes, and more preferably from 10 to 20 minutes). In particular, autoclaving is preferably carried out in the temperature range of 119° C. to 122° C. for a period of time ranging from 10 to 36 minutes. Further, the ready-to be infused solution of gemcitabine hydrochloride injection is subjected to stress studies to predict the shelf life of the product in aqueous media. Solutions of gemcitabine hydrochloride after autoclave at 121° C. for 15 minutes were stored at 25° C. and 40° C. at different stability conditions for a period of six-month. Data obtained from this study indicates that the solution is chemically as well as physically stable and the total degradants change over the period studied at 40 ° C. is less than 1%.

In one embodiment, terminal sterilization is performed by autoclaving the infusion containers filled with large volume solution of gemcitabine or its pharmaceutically acceptable salt in an aqueous vehicle. The autoclave is operated at a temperature ranging from 110° C. to 150° C. for a period of time of at least 5 minutes, preferably for a period of time ranging from 5 to 40 minutes. Specifically, the process involves autoclaving operated at a temperature in the range of 119° C. to 122° C. for a period of time ranging from 10 to 36 minutes.

Typically, the large volume infusion dosage form of the invention is prepared by steps of; dissolving gemcitabine or a pharmaceutically acceptable salt thereof in an aqueous vehicle to form a solution; adjusting the pH of the solution to 6.0 to 8.0; filling the solution into an infusion container; and subjecting the solution in the infusion container to terminal sterilization. It was found that the large volume dosage form obtained by such a process was stable and did not show any signs of crystallization under refrigerated conditions or at room temperature. The solution was chemically stable having impurity levels within the acceptable pharmacopoeial and ICH limits. The large volume infusion dosage form The pharmaceutical product of the invention is obtainable by subjecting a solution of gemcitabine, or a pharmaceutically acceptable salt thereof, to terminal sterilization; wherein the solution i) has a large volume ii) comprises gemcitabine or a pharmaceutically acceptable salt thereof in an aqueous vehicle and iii) is contained in a large volume infusion container. Typically, a pharmaceutical product obtainable from a process comprising the steps of; dissolving gemcitabine or a pharmaceutically acceptable salt thereof in an aqueous vehicle to form a solution; adjusting the pH of the solution to 6 to 8; filling the solution in an infusion container; and subjecting the filled infusion container to terminal sterilization.

Surprisingly, the inventors found that when the sterile pharmaceutical solutions were prepared using aseptic processing techniques, the solutions did not provide physical and chemical stability when stored at room temperature or refrigerated conditions. Without wishing to be bound by any theory, the inventors believe that it may be the effect of pressure and temperature during terminal sterilization, because of which the crystal seeding effect in gemcitabine hydrochloride, is suppressed. The surprising effect is evident from the results given in comparative examples. When the ready to infuse solution of present invention was filtered and aseptically filled in the infusion bags or vials(glass) without undergoing terminal sterilization, the solution when stored at 2° C. to 8° C. or at room temperature, showed the presence of crystals.

The following examples illustrate the scope of the present invention without any limitation thereto.

EXAMPLE 1-3

The ready-to infuse solution according to the present invention is prepared as follows.

TABLE 1

Composition of the ready-to-be-infused solution of the present invention

| Sr. No. | Ingredients | Example 1 | | Example 2 | | Example 3 | |
| --- | --- | --- | --- | --- | --- | --- | --- |
| | | mg/ml | % w/v | mg/ml | % w/v | mg/ml | % w/v |
| 1 | Gemcitabine hydrochloride (expressed as free base) | 10 | 1 | 12.5 | 1.25 | 15 | 1.5 |
| 2 | Sodium chloride | 9.0 | 0.9 | 9.0 | 0.9 | 9.0 | 0.9 |

TABLE 1-continued

Composition of the ready-to-be-infused solution of the present invention

| Sr. No. | Ingredients | Example 1 mg/ml | Example 1 % w/v | Example 2 mg/ml | Example 2 % w/v | Example 3 mg/ml | Example 3 % w/v |
|---|---|---|---|---|---|---|---|
| 3 | Sodium hydroxide | q.s | q.s | q.s | q.s | q.s | q.s |
| 4 | Hydrochloric acid | q.s | q.s | q.s | q.s | q.s | q.s |
| 5 | Water for injection | q.s to 1 ml | 100 ml | q.s to 1 ml | 100 | q.s to 1 ml | 100 |
|   | pH |  | 8.0 |  | 7.7 |  | 7.7 |

Specified quantity of water for injection was maintained at a temperature of 20° C. to 25° C. in a manufacturing tank. Nitrogen gas was purged for approximately 15-30 minutes. The nitrogen purging was stopped before addition of excipients and gemcitabine hydrochloride. Specified amount of sodium chloride was gradually added and the solution was stirred well for approximately 10 minutes. Complete solubilization of sodium chloride and clarity of solution was visually checked. The pH of the saline was checked.

Then the total quantity of gemcitabine hydrochloride was slowly added into bulk solution with continuous vortex stirring. The gemcitabine hydrochloride solution dispensing container was rinsed with sufficient water for injection and added to the bulk solution. The steps of rinsing were repeated till all the contents were transferred. The pH was adjusted at 7.70±0.2 using sufficient quantity of 10% w/v sodium hydroxide or 10% w/v hydrochloric acid. The volume was adjusted with water for injection. The solution was stirred for 10 minutes. The pH was maintained between 6.00 and 8.00. The solution was filtered through Ultipor N66 Cartridge Filter (0.2 micron-10 inch length).

The solution prepared as per the Table 1 and procedure described above, is filled into volumes to obtain the infusion container with gemcitabine hydrochloride which will provide 1600 mg. 1700 mg, 1800 mg and 2000 mg per bag, respectively, as described in Table 2 below.

TABLE 2

Large Volume infusion dosage form of gemcitabine solution at a concentration of 10 mg/ml (example 1)

| Capacity of the Infusion container (in ml) | Dose (in mg) | Fill volume (in ml) |
|---|---|---|
| 200 | 1600 | 160 |
| 200 | 1700 | 170 |
| 250 | 1800 | 180 |
| 250 | 2000 | 200 |

For 160 ml fill, standard fill volume was 175.51 ml (limit 172.00 ml to 179.02 ml). For, 170 ml fill standard fill volume was 185.71 ml (limit 182.00 ml to 189.42 ml).

For 180 ml fill standard fill volume was 195.92 ml (limit 192.00 ml to 199.84 ml, For 200 ml fill standard fill volume was 216.33 ml (limit 212.00 ml to 220.66 ml).

The filled Infusion bags were stoppered with autoclaved stoppers by using stopper feeding machine. The stoppered infusion bags were terminally sterilized in super heated water spray sterilizer as per terminal sterilization cycle (with a sterilization temperature of 121° C. and sterilization hold time of 15 minutes).

The infusion bags having solution of Example 1 were stored at 2-8° C. (refrigerated condition) and room temperature. The solutions were observed for any physical changes such as discoloration, clarity and presence or absence of crystals. The solutions were observed regularly over a period of 6 months. Results are given below in table 3.

TABLE 3

Physical stability study of ready-to-be-infused solution of example 1

| Sr. No. | Observation | Stability conditions 2° C.-8° C. | Stability conditions 25° C./(Room Temperature) |
|---|---|---|---|
| 1 | Crystal or particulate matter | No | No |
| 2 | Clarity | Clear | Clear |

The ready to be infused solution of example 1 was prepared as per the procedure described above but at different pH such as, pH 6.00, 7.00 & 8.00. The pH was adjusted using 10% Sodium hydroxide solution and/or 10% Hydrochloric acid solution. The initial sample of ready to infuse solution and samples stored at 40° C./75%RH for 2 month were analyzed for assay, related substance (%), pH, absorbance at 420 nm, % transmittance at 650 nm and osmolality. Results are given below in table 4.

TABLE 4

Chemical stability study of ready-to-be-infused solution of example 2 having different pH

| Test | | Limits | pH 6.00 Initial | pH 6.00 40° C./75% RH (2M) | pH 7.00 Initial | pH 7.00 40° C./75% RH (2M) | pH 8.00 Initial | pH 8.00 40° C./75% RH (2M) |
|---|---|---|---|---|---|---|---|---|
| Visual observation for presence of particulates | | clear | clear | Clear | Clear | Clear | Clear | clear |
| Assay of Gemcitabine (%) | | 90.0-110.0 | 103.75 | 101.99 | 102.33 | 100.66 | 102.99 | 101.99 |
| Related Substances (%) | Cytocine | NMT 0.10 | 0.001 | 0.003 | 0.003 | 0.002 | 0.001 | 0.003 |
| | Alpha Anomer | NMT 0.10 | 0.001 | 0.002 | 0.001 | 0.002 | 0.002 | 0.002 |
| | 2'-Deoxy-2',2' difluorouridine | NMT 2.50 | 0.077 | 0.366 | 0.008 | 0.301 | 0.011 | 0.287 |

TABLE 4-continued

Chemical stability study of ready-to-be-infused solution of example 2 having different pH

| | | pH 6.00 | | pH 7.00 | | pH 8.00 | |
|---|---|---|---|---|---|---|---|
| Test | Limits | Initial | 40° C./75% RH (2M) | Initial | 40° C./75% RH (2M) | Initial | 40° C./75% RH (2M) |
| Single Max Impurities | NMT 0.20 | 0.013 | 0.012 | 0.006 | 0.013 | 0.011 | 0.013 |
| Total Impurities (Excluding 2'-Deoxy-2',2'-difluorouridine) | NMT 0.30 | 0.059 | 0.063 | 0.051 | 0.059 | 0.071 | 0.059 |
| pH | — | 5.89 | 6.27 | 6.45 | 6.75 | 6.51 | 6.89 |
| Absorbance at 420 nm (AU) | NMT 0.1 | 0.000 | 0.001 | 0.000 | 0.002 | 0.001 | 0.002 |
| % Transmittance at 650 nm | NLT 95.0 | 99.821 | 99.934 | 99.794 | 99.945 | 99.648 | 99.963 |
| Osmolality (mOsm/kg) | 350-450 | 393 | 403 | 391 | 399 | 394 | 396 |

TABLE NO. 5

Stability results of Gemcitabine Hydrochloride Injection, 10 mg/ml, 160 ml
Fill volume & Pack: 160 ml in 200 ml infusion bag

| Condition | Description | Assay of Gemcitabine (%) | Related Substances (%) | | | | | pH | Absorbance at 420 nm | % Transmittance at 650 nm | Osmolality (mOsm/kg) |
|---|---|---|---|---|---|---|---|---|---|---|---|
| | | | Cytocine | Alpha Anomer | # | ## | ### | | | | |
| Limit | clear | 90.0-110 | NMT 0.10 | NMT 0.10 | NMT 2.50 | NMT 0.20 | NMT 0.30 | 6.00-8.00 | NMT 0.10 | NLT 95.0 | 350-450 |
| Initial | clear | 99.6 | 0.01 | 0.01 | 0.3 | 0.0 | 0.1 | 7 | 0 | 99 | 428 |
| 25° C./40% RH | | | | | | | | | | | |
| 1M | clear | 102 | 0 | 0.11 | 0.33 | 0.01 | 0.4 | 7.0 | 0 | 100 | 412 |
| 2M | clear | 99 | 0.01 | 0.01 | 0.34 | 0.01 | 0.1 | 6.6 | 0 | 100 | 394 |
| 3M | clear | 99 | BQL | 0.02 | 0.3 | 0.02 | 0.1 | 7.0 | 0 | 100 | 392 |
| 6M | clear | 100 | 0.05 | 0.01 | 0.4 | 0.01 | 0.05 | 6.9 | 0 | 99.9 | 393 |
| 30° C./35% RH | | | | | | | | | | | |
| 3M | clear | 99 | BQL | 0.02 | 0.33 | 0.02 | 0.1 | 7.1 | 0 | 100 | 396 |
| 6M | clear | 99 | 0.01 | 0.01 | 0.5 | 0.01 | 0.05 | 7.0 | 0 | 99.9 | 392 |
| 40° C./25% RH | | | | | | | | | | | |
| 1M | clear | 101 | 0.01 | 0.01 | 0.41 | 0.01 | 0.04 | 7.0 | 0.000 | 100. | 410 |
| 2M | clear | 99 | 0.01 | 0.01 | 0.44 | 0.01 | 0.05 | 6.7 | 0.000 | 100 | 394 |
| 3M | clear | 981 | BQL | 0.02 | 0.49 | 0.02 | 0.10 | 7.1 | 0.000 | 99.9 | 395 |
| 6M | clear | 99 | 0.01 | 0.01 | 0.97 | 0.01 | 0.05 | 7.1 | 0.000 | 99.9 | 392 |

\# = 2'-Deoxy-2',2' difluorouridine
\#\# = single maximum impurity
\#\#\# = total impurities (excluding 2'-Deoxy-2',2' difluorouridine)

The above data proves that the large volume dosage form of gemcitabine having a pH of about 6 to 8 is stable at room temperature. The shelf life of the product is estimated to be about two years. The ability of the formulation in Example 1 to withstand terminal sterilization was determined after extended autoclave cycles at 12° C. Autoclave cycle times studied ranged from 20 minutes up to 150 minutes.

COMPARATIVE EXAMPLE 1

The ready to be infused solution of example 1, 2 and example 3 was prepared according to the above procedure of example 1, where the infusion solution was sterilized by filtration (without terminal sterilization). The filtered solution was filled in either glass vials or sterile PVC bags. The filled containers were stored at 2-8° C. and 20-25° C. The solutions were evaluated for the stability i.e presence of crystals or particulate matter. Results of physical stability are given below in table 6.

TABLE 6

Physical stability study of ready-to-be-infused solution comparative example 1

| Example Number | Gemcitabine concentration In mg per ml | Physical Observation at following conditions | |
|---|---|---|---|
| | | 2° C.-8° C. | 20-25° C. |
| 1 | 10.0 | Crystals | Clear |
| 2 | 12.5 | Crystals | Clear |
| 3 | 15.0 | Crystals | Crystal in 3 weeks |

The above data shows the surprising finding that only the terminally sterilized solutions of gemcitabine are stable whereas the solutions aseptically filled into the container and stored at conditions which are generally required for parenteral products, show signs of instability such as presence of crystals or particulate matter.

The invention claimed is:

1. An infusion dosage form of gemcitabine comprising at least 100 ml of a stable solution of free gemcitabine or its pharmaceutically acceptable salt in an aqueous vehicle filled in an infusion container, wherein the solution is ready-to-be-infused, and wherein the injection dosage form is obtained by subjecting the solution of free gemcitabine or a pharmaceutically acceptable salt thereof in the filled infusion container to terminal sterilization in an autoclave.

2. The infusion dosage form as claimed in claim 1 wherein the infusion container is a polymeric single compartment container free of polyvinylchloride.

3. The infusion dosage form as claimed in claim 1 wherein the aqueous vehicle is free of co-solvents.

4. The infusion dosage form as claimed in claim 1 wherein the solution has a concentration of gemcitabine of 5 mg per ml to 20 mg per ml.

5. A kit comprising an infusion dosage form comprising at least 100 ml of a stable solution of free gemcitabine or its pharmaceutically acceptable salt in an aqueous vehicle filled in a polymeric infusion container covered with a secondary packaging system, wherein the solution is ready-to-be-infused, and wherein the injection dosage form is obtained by subjecting the solution of free gemcitabine or a pharmaceutically acceptable salt thereof in the filled infusion container to terminal sterilization in an autoclave.

6. The kit as claimed in claim 5, wherein the free gemcitabine or its pharmaceutically acceptable salt is present at a concentration of 10 mg per ml and is filled in volumes ranging from 100 ml to 300 ml.

7. The kit as claimed in claim 6, wherein the infusion container includes 160 ml of the stable solution of free gemcitabine or its pharmaceutically acceptable salt and provides a dose of 1600 mg of gemcitabine hydrochloride per container.

8. The kit as claimed in claim 6, wherein the infusion container includes 170 ml of the stable solution of free gemcitabine or its pharmaceutically acceptable salt and provides a dose of 1700 mg of gemcitabine hydrochloride per container.

9. The kit as claimed in claim 6, wherein the infusion container includes 180 ml of the stable solution of free gemcitabine or its pharmaceutically acceptable salt and provides a dose of 1800 mg of gemcitabine hydrochloride per container.

10. The kit as claimed in claim 6, wherein the infusion container includes 190 ml of the stable solution of free gemcitabine or its pharmaceutically acceptable salt and provides a dose of 1900 mg of gemcitabine hydrochloride per container.

* * * * *